United States Patent [19]
Tanimura et al.

[11] Patent Number: 5,985,554
[45] Date of Patent: *Nov. 16, 1999

[54] METHOD OF PROBING THE FUNCTION OF PROTEINS OR PEPTIDES ENCODED BY PARTIALLY SEQUENCED CDNAS BY INHIBITING PROTEIN SYNTHESIS WITH ANTISENSE OLIGONUCLEOTIDES

[75] Inventors: Hiroshi Tanimura, Tsukuba; Masaki Hosoya, Tsuchiura, both of Japan

[73] Assignee: Takeda Chemical Industries, Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/550,120

[22] Filed: Oct. 30, 1995

[30] Foreign Application Priority Data

Nov. 2, 1994 [JP] Japan .................................. 6-269417

[51] Int. Cl.$^6$ .............................. C12Q 1/68; C12P 21/00; C07M 21/04; A61K 48/00
[52] U.S. Cl. .......................... 435/6; 435/69.1; 536/24.5; 514/44
[58] Field of Search .......................... 536/24.5; 435/69.1, 435/6; 514/44

[56] References Cited

U.S. PATENT DOCUMENTS 5,405,772  4/1995  Ponting .............................. 435/240.31

OTHER PUBLICATIONS

Gudkov et al. (1994) Proc. Natl. Acad. Sci. USA 91:3744–3748.
Stull et al. (1992) Nucleic Acids Research 20:3501–8.
Ghosh et al, "Oligodeoxynucleotides as antisense inhibitors of gene expression", In: Progress in Nucleic Acid Research and Molecular Biology, vol. 42, pp. 79–126, 1992.
Xiao et al, "Generation of an ilv bradytrophic phenocopy in yeast by antisense RNA", Current Genetics 13:283–289, 1988.
Keith et al, "Inhibition of bcl–2 with Antisense oligonucleotides induces apoptosis and increases the sensitivity of AML blasts to ARA–C", Leukemia 9:131–138, Jan. 1995.
Gerald Zon, "Oligonucleotide Analogues as Potential Chemotherapeutic Agents", Pharmaceutical Research, vol. 5, No. 9, pp. 539–549, 1988.
Stein et al., "Oligodeoxynucleotides as Inhibitors of Gene Expression: A Review", Cancer Research 48, pp. 2659–2668, May 15, 1988.
Uhlmann et al., "Antisense Oligonucleotides: A New Therapeutic Principle", Chemical Reviews, vol. 90, No. 4, pp. 544–584, Jun. 1990.
Weintraub et al., "Anti–sense RNA as a Molecular Tool for Genetic Analysis", Trends in Genetics, pp. 22–25, Jan. 1985.
Cabrera et al., "Phenocopies Induced with Antisense RNA identify the Wingless Gene", Cell, vol. 50, pp. 659–663, Aug. 14, 1987.
Inoue et al., "Evolutionary Conservation of the Insulinoma Gene Rig and Its Possible Function", Proc. Natl. Acad. Sci. USA vol. 84, pp. 6659–6662, Oct. 1987.
Heikkila et al., "A c–myc Antisense Oligodeoxynucleotide Inhibits Entry into S Phase but not Progress from $G_0$ to $G_1$", Nature vol. 328, pp. 445–449, Jul. 30, 1987.
Harrison, "Antisense: Into the Brain", The Lancet, vol. 342, pp. 254–255, Jul. 31, 1993.
Wahlestedt et al., "Antisense Oligodeoxynucleotides to NMDA–R1 Receptor Channel Protect Cortical Neurons from Excitotoxicity and Reduce Focal Ischaemic Infarctions", Letters to Nature, vol. 363, pp. 260–263, 1993.
Goodchild, "Conjugates of Oligonucleotides and Modified Oligonucleotides: A Review of Their Synthesis and Properties", Bioconjugate Chemistry, vol. 1, No. 3, pp. 165–187, May/Jun. 1990.
Osen–Sand et al., "Inhibition of Axonal Growth by SNAP–25 Antisense Oligonucleotides in vitro and in vivo", Letters to Nature, vol. 364, pp. 445–448, 1993.

*Primary Examiner*—Jeffrey Fredman
*Attorney, Agent, or Firm*—Wenderoth, Lind & Ponack, L.L.P.

[57] ABSTRACT

The present invention provides a method for an efficient elucidation of the function of a protein or peptide encoded coded by cDNA, in which only a partial sequence of the protein or peptide is elucidated and the function is unknown. The method adding an antisense oligonucleotide complementary to the partial sequence of the cDNA to an evaluating system for the biological function, whereby the protein or the peptide encoded by said cDNA can be expressed. Accordingly, the function of the protein/peptide encoded by a cDNA can be efficiently elucidated even in a stage where only a partial sequence of said cDNA is analyzed.

9 Claims, 2 Drawing Sheets

(FULL-LENGTH cDNA WHEREIN THE FUNCTION THEREOF IS UNKNOWN)

5'                                                                                                          3'

(EMBODIMENT 1; ▭ : CLONED cDNA AND ▭ : SEQUENCED PARTIAL NUCLEOTIDE REGION)

(EMBODIMENT 2; ▭ : CLONED cDNA AND ▭ : SEQUENCED PARTIAL NUCLEOTIDE REGION)

(EMBODIMENT 3; ▭ : CLONED cDNA AND ▭ : SEQUENCED PARTIAL NUCLEOTIDE REGION)

SEQUENCE LISTING (1) GENERAL INFORMATION:

(iii) NUMBER OF SEQUENCES:  14

(2) INFORMATION FOR SEQ ID NO:1:

(i) SEQUENCE CHARACTERISTICS:
       (A) LENGTH:  100 bases
       (B) TYPE:  nucleic acid
       (C) STRANDEDNESS:  double
       (D) TOPOLOGY:  linear (ii) MOLECULE TYPE: cDNA (xi) SEQUENCE DESCRIPTION: SEQ ID NO:1:

GTAAGAGTTT GTGGAAGGAT TAACCTGCGC GCGCCGGGGT GGGTGCCTGT GCGGGGCGCG    60

CGGGGCGGGC GGCGGTGGGT GCCCGTGGGG GCCAGGGTGA    100

(2) INFORMATION FOR SEQ ID NO:2:

(i) SEQUENCE CHARACTERISTICS:
       (A) LENGTH:  15 bases
       (B) TYPE:  nucleic acid
       (C) STRANDEDNESS:  single
       (D) TOPOLOGY:  linear (ii) MOLECULE TYPE: other nucleic acid, synthetic DNA (xi) SEQUENCE DESCRIPTION: SEQ ID NO:2:

TCCACAAACT CTTAC    15

(2) INFORMATION FOR SEQ ID NO:3:

(i) SEQUENCE CHARACTERISTICS:
       (A) LENGTH:  15 bases
       (B) TYPE:  nucleic acid
       (C) STRANDEDNESS:  single
       (D) TOPOLOGY:  linear (ii) MOLECULE TYPE: other nucleic acid, synthetic DNA (xi) SEQUENCE DESCRIPTION: SEQ ID NO:3:

CCCCGCGCGC CCCGC                                                        15

(2) INFORMATION FOR SEQ ID NO:4:

(i) SEQUENCE CHARACTERISTICS:
        (A) LENGTH:  15 bases
        (B) TYPE:  nucleic acid
        (C) STRANDEDNESS:  single
        (D) TOPOLOGY:  linear (ii) MOLECULE TYPE: other nucleic acid, synthetic DNA (xi) SEQUENCE DESCRIPTION: SEQ ID NO:4:

CTGGCCCCCA CGGGC                                                        15

(2) INFORMATION FOR SEQ ID NO:5:

(i) SEQUENCE CHARACTERISTICS:
        (A) LENGTH:  15 bases
        (B) TYPE:  nucleic acid
        (C) STRANDEDNESS:  single
        (D) TOPOLOGY:  linear (ii) MOLECULE TYPE: other nucleic acid, synthetic DNA (xi) SEQUENCE DESCRIPTION: SEQ ID NO:5:

CATTCTCAAA CACCT                                                        15

(2) INFORMATION FOR SEQ ID NO:6:

(i) SEQUENCE CHARACTERISTICS:
        (A) LENGTH:  15 bases
        (B) TYPE:  nucleic acid
        (C) STRANDEDNESS:  single
        (D) TOPOLOGY:  linear (ii) MOLECULE TYPE: other nucleic acid, synthetic DNA (xi) SEQUENCE DESCRIPTION: SEQ ID NO:6:

CGCCCCGCGC GCCCC                                                        15

(2) INFORMATION FOR SEQ ID NO:7:

(i) SEQUENCE CHARACTERISTICS:
        (A) LENGTH:  15 bases
        (B) TYPE:  nucleic acid
        (C) STRANDEDNESS:  single
        (D) TOPOLOGY:  linear (ii) MOLECULE TYPE: other nucleic acid, synthetic DNA (xi) SEQUENCE DESCRIPTION: SEQ ID NO:7:

CGGGCACCCC CGGTC                                                        15

(2) INFORMATION FOR SEQ ID NO:8:

(i) SEQUENCE CHARACTERISTICS:
        (A) LENGTH:  178 bases
        (B) TYPE:  nucleic acid
        (C) STRANDEDNESS:  double
        (D) TOPOLOGY:  linear (ii) MOLECULE TYPE: cDNA (xi) SEQUENCE DESCRIPTION: SEQ ID NO:8:

CGAGTGGACA GTGGCAGGCG GTGACTGAAT CTCCAAGTCT GGAAACAATA GCCAGAGATA       60

```
GTGGCTGGGA AGCACCATGG CCAGAGTCCT GCAGCTCTCC CTGACTGCTC TCCTGCTGCC      120

TGTGGCTATT GCTATGCACT CTGACTGCAT CTTCAAGAAG GAGCAAGCCA TGTGCCTG       178
```

(2) INFORMATION FOR SEQ ID NO:9:

(i) SEQUENCE CHARACTERISTICS:
        (A) LENGTH: 15 bases
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:9:

```
GCCACTGTCC ACTCG                                                      15
```

(2) INFORMATION FOR SEQ ID NO:10:

(i) SEQUENCE CHARACTERISTICS:
        (A) LENGTH: 15 bases
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:10:

```
TCTGGCCATG GTGCT                                                      15
```

(2) INFORMATION FOR SEQ ID NO:11:

(i) SEQUENCE CHARACTERISTICS:
        (A) LENGTH: 15 bases
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:11:

```
GAAGATGCAG TCAGA                                                      15
```

(2) INFORMATION FOR SEQ ID NO:12:

(i) SEQUENCE CHARACTERISTICS:
        (A) LENGTH: 15 bases
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:12:

```
GCTCACCTGT CACCG                                                      15
```

(2) INFORMATION FOR SEQ ID NO:13:

(i) SEQUENCE CHARACTERISTICS:
        (A) LENGTH: 15 bases
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:13:

```
TCGTGGTACC GGTCT                                                      15
```

(2) INFORMATION FOR SEQ ID NO:14:

(i) SEQUENCE CHARACTERISTICS:
        (A) LENGTH: 15 bases
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:14:

AGACTGACGT AGAAG                        15

METHOD OF PROBING THE FUNCTION OF PROTEINS OR PEPTIDES ENCODED BY PARTIALLY SEQUENCED CDNAS BY INHIBITING PROTEIN SYNTHESIS WITH ANTISENSE OLIGONUCLEOTIDES

BACKGROUND OF THE INVENTION

1. Field of the Invention

With an object of elucidating and analyzing the function of novel DNA such as cDNA which has a possibility of being associated with certain types of diseases in a specific organ or tissue and wherein the nucleotide sequence of said DNA is partially sequenced, the present invention relates to a method for probing the function of said cDNA using an antisense oligonucleotide complementary to the partial sequence of said cDNA. More particularly, the present invention relates to a method for efficiently probing the function of a protein encoded by a DNA wherein the nucleotide sequence of said DNA is partially sequenced, e.g., obtained by a random decoding of cDNA library and the like, whereby pharmaceuticals, diagnostic agents, chemical reagents, etc. can be developed.

2. Description of Related Art

At present, it is assumed that there are several tens of thousands of genes which code for proteins and peptides in the cells of animals including human being. In a human genome project which has been proceeded in the field of genetic engineering, revelation of the primary structure of proteins encoded by all human genes is one of the most important targets. However there is a problem that, even if the nucleotide sequence of the genome is revealed, the primary structure of the protein encoded by said revealed sequence cannot be determined because, usually, there are many intron regions in genes.

In addition, even if the structure of each gene is determined, it does not help elucidate life phenomena, particularly various biological phenomena based upon the function of the protein encoded by human gene until it becomes clear what kind of functions such many genes have. Furthermore, it is useless to developing useful pharmaceuticals or non-contributable to the therapy of various diseases and illnesses. As a result of development of biochemical and molecular biological techniques, structures and functions of some proteins and peptides have been revealed already. The actual status is, however, that few genes have ever been isolated and revealed in terms of the structure and function of the coded proteins. Most of the rest have not been imagined at all even for the types and the numbers thereof. It is expected that, among such unknown proteins and peptides, some will be targets for the development of unique pharmaceuticals, diagnostic agents and chemical reagents. Thus, it is very important to know not only the sequence information of gene but also the functions of said gene, particularly the functions of the proteins encoded by the gene.

According to the conventional methods, however, a substantial amount of labor and cost is required for finding out novel proteins and peptides and also for elucidating their structures and functions. Therefore, it has not been possible to investigate them in an efficient manner. In brief, in such conventional methods, it is necessary to find a biological function in which novel protein/peptide is thought to participate. However, when the known assessment system for biological functions is utilized, discrimination with known protein/peptide is difficult and, preferably, it is necessary to find a novel biological function. Consequently, most of endeavors for finding novel proteins and peptides have been devoted to the investigation of such novel biological functions. However, even if novel proteins/peptides can be found by chance, they are obtained in a very small amount in most of the cases. In view of the above, it is necessary that protein is purified paying much labor, that a partial amino acid sequence is determined and that, based upon the resulting sequence, cDNA which codes for said protein/peptide is cloned. Although an expression cloning using, as an index, a biological function has been conducted, there has been little cases of success. As such, it has been only possible to utilize it to the development of pharmaceuticals, diagnostic agents and chemical reagents as a result of a series of voluminous and complicated studies from finding of the function until cloning of cDNA which may require much labor and cost. Under such circumstances, it is not easy to investigate many proteins and peptides. Furthermore, such a means cannot be utilized for the case where the biological function is entirely unknown.

In recent years, there has been a rapid progress in genetic engineering techniques and the studies have been carried out in an effective manner but, in spite of that, the technique such as a cDNA cloning requires skill and experience. Especially in the case of sequencing of cloned cDNA, it should be conducted by hand using radioisotopes (RI). However, as a result of a recent development and improvement in analyzers for nucleotide sequences (DNA sequencers), it has been possible to conduct an analysis of nucleotide sequences without the use of RI and, moreover, in an automatic manner. As such, the analysis of nucleotide sequences which was conducted only by the use of cloned cDNA fragments can now be carried out using much more cDNA fragments as objects. Thus, if the nucleotide sequences can be elucidated one after another by such a means and if the structures of the proteins and peptides encoded thereby can be clarified, it will be now possible to effectively achieve the novel proteins and peptides.

In view of the above, projects (a representative example is a human genome project) in which only the partial sequence of cDNA library is randomly decoded and the resulting sequences are analyzed after putting in a database have been carried out throughout the world. As a result, when a cDNA which has a homology with the cDNA coding for known protein/peptide is obtained, functions of the protein/peptide encoded by said cDNA can now be presumed to a considerable extent from the resulting sequence information only. In fact, subtypes of known proteins and peptides have been successively elucidated by means of such an approach.

However, it is usual that most of cDNA's do not exhibit a homology which is sufficient for estimating the function with the cDNA which codes for known proteins and peptides. Therefore, even if a lot of partial sequences of cDNA are determined, there is very little possibility of success in revealing the function. Accordingly, the actual present status is that there have been many accumulations of partial sequences of cDNA wherein the sequences themselves are novel but neither structure nor function encoded thereby are elucidated. It is not easy to elucidate the structure and function of coded proteins/peptides based on the partial nucleotide sequence of novel cDNA.

For example, in the case of presumption of an amino acid sequence from a nucleotide sequence of cDNA having novel sequence, there are six translation frames which have a possibility of coding for the protein or peptide. When there is entirely no nucleotide sequence such as TGA, TAG or TAA which is supposed to be a translation termination codon at the downstream from ATG (which is supposed to be a translation initiation codon) or at the upstream from TGA, TAG or TAA (which is supposed to be a translation termination codon) in the above six frames, then a possibility that the amino acid sequence encoded by said frame is an amino acid sequence of the protein/peptide encoded by said cDNA will be strongly suggested. There is also a possibility that, when there is entirely no nucleotide sequence such as TGA, TAG or TAA supposed to be a translation termination codon, all of those translation frames will code for the peptide or protein. In addition, when the nucleotide sequence is partially substituted or dropped due -to an error in analyzing the nucleotide sequence, there is a possibility of substitution of the partially coded amino acid sequence or of a shift of the translation frame. Accordingly, at present, it is possible to decide the correct amino acid sequence of the protein/petide encoded by said cDNA only when the cDNA having a full-length translation frame (an area between the translation initiation codon [ATG] at the upstream and that [TGA/TAG/TAA] at the downstream in a single translation frame) is available and its entire nucleotide sequence is determined.

Only when such problems are overcome, it is possible to chemically synthesize the partial peptide of said protein/peptide or to prepare said protein/peptide in full by means of genetic engineering in large quantities. For example, it is possible to prepare antiserum/antibody against said protein/peptide or to label it with a suitable fluorescent substance or radioisotope. However, investigation of the function requires many additional difficulties and labor.

In addition, it has been known to investigate the function by an introduction to cultured cells or transgenic animals either as they are or after a modification followed by an excessive expression or a destruction but all of those need a lot of cost and time and they are not able to be commonly applied to many cDNAs.

As mentioned hereinabove, although it is easy to decide the partial sequence of cDNA, it is still difficult to decide the function of the protein/peptide encoded thereby.

Now, the role played by cDNA will be considered. Since cDNA is an artificially synthesized DNA using a reverse transcriptase wherein mRNA is used as a template, it has a nucleotide sequence complementary to mRNA. Accordingly, unlike genome DNA wherein protein-coding regions are interrupted by intervening sequences (introns), it is possible to decide the amino acid sequence of the coded protein by deciding the nucleotide sequence of cDNA. The characteristic features of cDNA as compared with genome DNA are (1) since there is no intron, the primary structure of the coded protein can be determined immediately when the nucleotide sequence is sequenced; (2) since its size is small, it can be handled easily; and (3) when a suitable promoter or the like can be utilized, it can be expressed in all types of cells from eukaryotic to prokaryotic ones.

In addition, although it is not possible to check from the structure when and in which cell it is expressed in the case of genome, an expression in the cell can be surely proved in the case of cDNA upon the completion of cloning. Accordingly, such a tissue specificity is one of the very useful information for checking the function of the gene. When such a property of cDNA is taken into consideration, the importance of the role played by cDNA in a human genome project can be clarified.

Now, in the current technology, cDNA whose structure is completely analyzed is essential for analysis of structure and function of the gene which is a functional unit of genome. However, in the current art, it is still difficult to obtain a full-length cDNA clone. Moreover, it is substantially impossible to check the function directly from the cDNA whose structure is elucidated only partly. Accordingly, so far as the conventional investigating means for the function analysis is utilized, the current status is that initiation of the study for elucidating its function is not possible from the information for the partial sequence only of the voluminous cDNA library and that will be a large problem in proceeding the study. In addition, even when the structure of the full-length cDNA is elucidated, much difficulty and labor are needed for construct the expression system which effectively expresses the desired protein from said information only. In fact, at present, any researching means for investigating the function from the cDNA sequence information wherein only partial sequence is known has not been established yet.

Now, an art in which a repression of expression of gene is conducted by a chemical synthesized oligonucleotide having a complementary sequence to a sequence in a domain specific to said gene or mRNA transcribed from said gene is widely known as an antisense method (G. Zon, Pharmaceutical Res., 5(9). 539 (1988); C. A. Stein et al., Cancer Res., 48, 2659(1988); E. Uhlman et al., Chemical Rev., 90(4), 543 (1990); J. Goodchild, Bioconjugate Chem., 1(3), 165 (1990)). Attempts for conducting the repression of expression of virus gene, oncogenes, etc. using such an antisense oligonucleotide has been investigated particularly in detail. The antisense oligonucleotide used therefor has a disadvantage that it is easily decomposed by a hydrolase such as nuclease when the oligonucleotide is in a natural phosphate structure. Therefore, in order to improve the stability against such an enzyme, various nucleotide derivatives which are chemically modified in phosphate groups or sugar-hydroxyl groups have been developed. An example of derivatives in which a phosphate group in nucleotide is modified is a phosphorothioate (F. Eckstein, Angew. Chem., 6, 431 (1983); F. Eckstein et al., Biochemistry, 23, 3443 (1984); J. W. Stec et al., J. Am. Chem. Soc., 106, 6077 (1984); F. Eckstein et al., Ann. Rev. Biochem., 54, 367 (1985)), a methylphosphonate (P. S. Millar et al., Biochemistry, 18, 5134 (1979); P. S. Millar et al., Biochimie, 67, 769 (1985); P. O. P. Ts'O et al., Ann. N. Y. Acad. Sci., 507, 220 (1988)), etc.

In addition, a method of methylating a 2'-hydroxyl group has been proposed as one of the attempts for improving the stability by modifying the 2'-hydroxyl group of a ribose ring which is a constituting unit of the nucleotide (Y. Furukawa et al., Chem. Pharm. Bull., 13, 1273 (1965); E. Ohtsuka et al., Nucleic Acids Res., 15, 6131 (1987)). Among those, a phosphorothioate derivative (which completely covers the mRNA to be treated and, thereafter, is able to become a substrate hydrolyzable with RNase H) is fully capable of achieving an antisense effect, is stable to hydrolase or the like and exhibits a relatively low cell toxicity and, accordingly, it is used as the best antisense derivative at this moment. As such, phosphorothioate derivatives have been widely utilized as an effective means for repression of expression of genes.

At present, this method of elucidating the function of cDNA by means of an antisense method using an antisense oligonucleotide such as said phosphorothioate derivatives was reported to be used with an object of confirming the presumed function of said cDNA after presuming almost all of the functions of the cDNA by a homology investigation or the like of the sequence information with the known gene as a result of analysis of full-length nucleotide sequence of cDNA (H. Weintraub et al., Trends in Genetics, 1, 22 (1985); C. V. Cabrera et al., Cell, 50, 659 (1987); C. Inoue et al., Proc. Natl. Acad. Sci. USA, 84, 6659 (1987); R. Heikkila et al., Nature, 328, 445 (1987); P. Harrison et al., Lancet, 342, 254 (1993); C. Wahlestdt et al., Nature, 363, 260 (1993); A. Osensand et al., Nature, 364, 445 (1993)). However, there has been no case of utilization of the antisense method for elucidating the function of novel cDNA wherein only partial sequence is known.

As such, the means which have been known for investigating the function from the structure of gene are:

(1) a method in which the function which is intensified by an excessive expression of the gene is analyzed; and (2) a method in which a homology with known genes using is investigated by computers.

In elucidating the function of cDNA using the method of (1), it is unavoidable to firstly clone the cDNA of a full length for completely coding for protein so that all of its sequence information is checked. In constructing the expression system wherein the desired protein can be efficiently expressed from such an information, a lot of difficulties and labor are needed.

In the method (2), it is possible to investigate the function from the information on a partial sequence provided for the highly homologous sequence, but if it remains to show the lower homologous sequence, an elucidation of the function of cDNA from said cDNA wherein only the partial sequence is known (that is an object of the present invention) is not possible.

SUMMARY OF THE INVENTION

An object of the present invention is to provide a method for an efficient elucidation of the function of cDNA wherein the nucleotide sequence of said DNA is partially sequenced (particularly the function of protein/peptide encoded by said cDNA) utilizing an antisense oligonucleotide which is manufactured based upon said partial sequence of said cDNA. More preferably, an object of the present invention is to provide a method for an efficient elucidation of the function of protein/peptide encoded by the cDNA wherein its sequence is randomly determined from a cDNA library or the like.

The present inventors have conducted an extensive study for solving the above-mentioned problems and have found a novel method for efficiently probing the function of proteins and peptides encoded by the cDNA (wherein a nucleotide of said DNA is partially sequenced) by preparing an antisense oligonucleotide based upon said partial sequence of said cDNA followed by using said antisense oligonucleotide. The principal concept of the present invention is a method for probing the function of protein and peptide encoded by each cDNA at the stage where a nucleotide of said DNA is partially sequenced. Thus, it is a novel probing method which is entirely non-obvious from the conventional methods.

As a result of the use of the method of the present invention in which the antisense oligonucleotide is utilized, functions of many proteins and peptides wherein neither structure nor function is known can be efficiently elucidated at the stage when a nucleotide of said protein-coding DNA is partially sequenced. The method for probing the functions in accordance with the present invention is a particularly important means for the research in a project in which partial nucleotides of a cDNA library are randomly sequenced and the retrieval is carried out by putting the resulting sequence into a database. In addition, when the function of novel protein/peptide can be revealed by means of the present invention, that will be a very useful information for the development of unique pharmaceuticals, diagnostic agents and chemical reagents.

Accordingly one aspect of the present invention is:

(1) a method for probing the function of a protein encoded by a cDNA wherein a nucleotide of said cDNA is partially sequenced, which comprises assessing the change of biological actions when an antisense oligonucleotide substantially complementary to the partial nucleotide sequence to an assessment system for biological functions thereof; and (2) a method according to (1) in which said partial nucleotide sequence is a segment positioned at the 5'-terminal region of a full-length nucleotide sequence of said cDNA.

Another aspect of the present invention is:

(3) a method according to (1) in which said antisense oligonucleotide is selected from the group consisting of polydeoxynucleotides containing 2'-deoxy-D-ribose, polyribonucleotides containing D-ribose, any other type of polynucleotide which is an N-glycoside of a purine or pyrimidine base, or other polymers containing nonnucleotide backbones including protein nucleic acids and synthetic sequence specific nucleic acid polymers commercially available or nonstandard linkages, providing that the polymers contain nucleotides in a configuration which allows for base pairing and base stacking such as is found in DNA and RNA;

(4) a method according to (1) wherein said antisense oligonucleotide is selected from the group consisting of methyl phosphonates, phosphorotriesters, phosphoramidates, carbamates, phosphorothioates, and phosphorodithioates; and (5) a method for probing the function of a protein encoded by a cDNA wherein a nucleotide of said cDNA is partially sequenced but no biological action thereof is known, which comprises:

(a) designing and preparing an antisense oligonucleotide substantially complementary to the partial nucleotide sequence of said cDNA;

(b) conducting a comparison among:

(i) at least one case wherein the biological function of said cDNA is assessed in the presence of said antisense oligonucleotide, (ii) at least one case wherein the biological function thereof is assessed in the presence of a reverse sequenced oligonucleotide, and (iii) at least one case wherein the biological function thereof is assessed under conditions free from said antisense oligonucleotide; and (c) determining the function of said cDNA based on the difference obtained by the assessment step (b).

Still another aspect of the present invention is:

(6) a method for probing the function of a protein encoded by cDNA wherein a nucleotide of said DNA is partially sequenced by techniques including a random decoding, etc. of the cDNA library, etc., which comprises the following steps:

(a) preparing an antisense oligonucleotide which is substantially complementary to said partial sequence of the cDNA, (b) then adding said antisense oligonucleotide to an assessment system for the biological function wherein the protein encoded by said cDNA is expressible and (c) evaluating the resulting change in said biological function obtained thereby;

(7) a method according to any of (1) to (6) in which the assessment system for the biological function wherein the protein or peptide encoded by said cDNA can be expressed is a cell having a possibility of expressing the protein or peptide encoded by said cDNA;

(8) a method according to any of (1) to (7) in which the assessment system for the biological function wherein the protein or peptide encoded by said cDNA is a cell which is capable of expressing the mRNA having a nucleotide sequence complementary to said cDNA;

(9) a method according to any of (1) to (8) in which the cell used for the assessment system is a cell culture;

(10) a method according to any of (1) to (9) in which the cell used for the assessment system is a cell selected from the group consisting of nerve cell, bone cell, muscle cell, blood vessel cell, endocrine cell, lymphocyte, reticuloendothelial cell and the like or, more particularly, a selected from the group consisting of smooth muscle cell, endothelial cell, fibroblast, epithelial cell, blood cell and the like;

(11) a method according to any of (1) to (10) in which the cell used for the assessment system is a cell derived from the tissues which constitute epidermis, mucous membrane, exocrine gland, endocrine gland, lung, digestive organ, urinary/genital gland, genital cell, liver, fat tissue, connective tissue, blood vessel, muscle, hematocyte, bone marrow, nerve, etc. and is an established cell strain or a primary cultured cell from the above normal or tumorized tissue;

(12) a method according to any of (1) to (11) in which the change of biological actions is a promotion or an inhibition of the production of enzyme, extracellular matrix and adhesion molecule, transcription controlling factor, growth factor, hormone, cytokine, differentiation/induction factor, chemotaxic factor, neurotransmitter and the like in the cell;

(13) a method according to any of (1) to (12) in which the change of biological actions is a production of a factor related to various amplifications and differentiations or a gene-expression regulating factor such as growth factor, hormone, cytokine, a chemotaxic factor such as a factor capable of promoting the migration of leukocyte, protein capable of increasing the phagocytosis or bacteriocidal ability of leukocyte, lymphocyte growth factor, T cell activating factor, T cell growth factor, antigen-specific inhibiting factor specifically acting on an immune system, antigen-nonspecific inhibiting factor, etc. as well as various gene products including various enzymes and regulatory factors and also a promotion or an inhibition of the production of said gene products in cells;

(14) a method according to any of (1) to (11) in which the change of biological actions is a change on the surface of the cell, such as production of receptor protein or production of adhesion molecules, or a change outside the cell, such as a formation of extracellular matrix;

(15) a method according to any of (1) to (11) in which the change of biological actions is:

an opening-closing of ion channel, a change in the cell membrane potential or a change in the intracellular or extracellular pH caused thereby, or an activation or inactivation of an intracellular information delivery system mediated by various receptor proteins; and a primary promotion or inhibition of production of various second messengers (such as cAMP, cGMP, inositol phosphate metabolites, diacylglycerol, intracellular calcium ion and arachidonic acid metabolites) as well as secondarily induced phosphorylation, dephosphorylation, etc. of various proteins;

(16) a method according to any of (1) to (11) in which the change of biological actions is a change in the second messenger (such as liberation of arachidonic acid, liberation of acetylcholine, liberation of $Ca^{+2}$, generation of cAMP, generation of cGMP, production of inositol phosphate metabolites, change in cell membrane potentials, phosphorylation of protein, activation of c-fos and change in pH);

(17) a method according to any of (1) to (11) in which the change of biological actions is a morphological change of cells such as elongation of neutrite, shrinking or expansion of the cell, generation and disappearance of intracellular granules, etc.;

(18) a method according to any of (1) to (17) which is a series of processes comprising:
 (a) sequencing a partial nucleotide sequence thereof,
 (b) analyzing information on the nucleotide sequence,
 (c) designing and preparing an antisense oligonucleotide, and
 (d) assessing the biological function;

(19) a pharmaceutical or diagnostic composition or chemical reagent comprising an effective amount of a protein whose function is elucidated by a method according to any of (1) to (18);

(20) a method for developing a pharmaceutical or diagnostic composition or chemical reagent which comprises using an assessment system for the biological function of the protein elucidated by a method according to any of (1) to (18);

(21) a pharmaceutical or diagnostic composition or chemical reagent comprising an effective amount of an antisense oligonucleotide per se prepared in a probing method according to any of (1) to (18);

(22) a method according to any of (1) to (17), in which the assessment step (b) is carried out in a system capable of detecting a biological response relying on said cDNA;

(23) a method according to any of (1) to (18), in which said detecting system is an in vitro system; and

(24) a method according to any of (1) to (18), in which said detecting system is an in vivo system.

The characteristic feature of the present invention is that, in a method for elucidating or probing the function of target cDNA whose function is ambiguous, especially unknown, (particularly for elucidating or investigating the function of a protein (including a peptide) encoded by target cDNA wherein a nucleotide of said DNA is partially sequenced), an antisense technique using an antisense oligonucleotide which is complementary (hybridizable) to the partial sequence of the target cDNA is utilized whereby the function of said cDNA (particularly, the function of the protein/peptide encoded by said cDNA) can be efficiently elucidated in the stage where only the partial sequence is known (particularly, without sequencing the entire nucleotide sequence of the cDNA). Said antisense oligonucleotide has a characteristic feature that the oligonucleotide which is complementary (hybridizable) to all or part of said partial sequence can be used. The probing method according to the present invention has a characteristic feature that the function of said cDNA can be elucidated prior to the sequencing of full-length nucleotide sequence of said cDNA and has another characteristic feature that it is suitable for conducting the elucidation of function of cDNA as a series of automated system.

DETAILED DESCRIPTION OF THE PREFERRED EMBODIMENT

Figure 1:
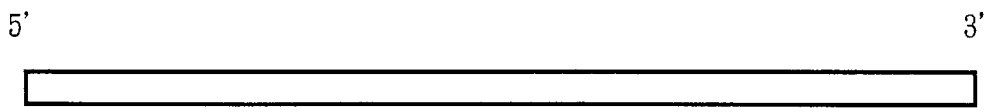
FIG. 1 depicts a model of cDNA wherein a nucleotide of said DNA is partially sequenced in a probing method of the present invention.
Figure 1:
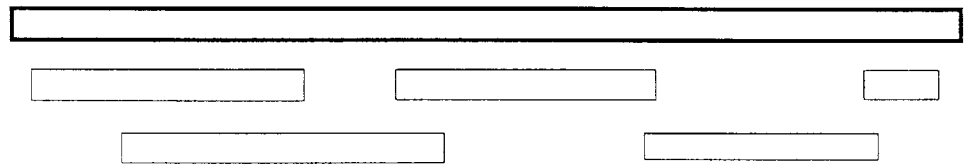
Figure 1:
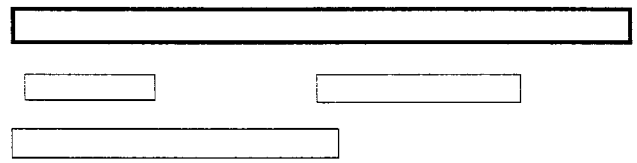
Figure 1:
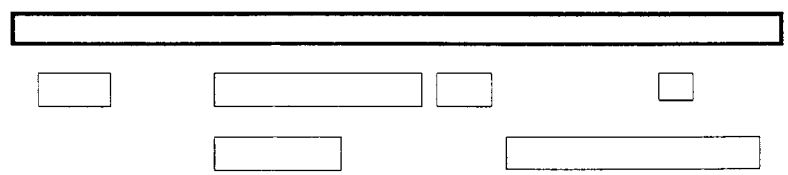

According to the present invention, a effective method for probing the function of said cDNA is provided by using an antisense oligonucleotide complementary to the partial sequence of said cDNA, particularly the cDNA wherein a nucleotide of said DNA is partially sequenced. In an embodiment of the present invention, a efficient method for elucidating or investigating the function of a protein encoded by a DNA wherein a nucleotide of said DNA is partially sequenced is provided based upon the partial sequence, e.g., obtained by a random decoding of cDNA library and the like, whereby pharmaceuticals, diagnostic agents, chemical reagents, etc. can be developed.

The phrase reading "cDNA in which a nucleotide of said DNA is partially sequenced" used herein stands for cDNA which completely codes for certain protein/peptide or cDNA which partially codes for certain protein/peptide where only a part of the full-length nucleotide sequence of said cDNA is sequenced. The term "protein" refers to a protein encoded by the target cDNA, a peptide encoded by the target cDNA, a salt thereof, a fragment or conjugated derivative thereof, a modified derivative thereof and the like.

When, for example, a cDNA library prepared by inserting a cDNA fragment into a phage or plasmid vector is subjected to a random sequencing analysis for nucleotide sequences, it is usual that the sequencing operation is conducted using a primer for the sequencing prepared based upon the partial nucleotide sequence of the vector at the region whereinto the cDNA is inserted. As such, the nucleotide sequence of one terminal region of the cDNA area can be sequenced. Usually, a single nucleotide sequencing makes a sequence information for several hundreds of base pairs available but, in many cases, the length of the cDNA fragment is longer than the above. When the inserted direction of the cDNA is regulated by a suitable method, the resulting partial sequence of the cDNA is a nucleotide sequence of the 5'-terminal area of said cDNA fragment. Then the determined partial sequence data thereof can be registered and controlled in the database using a computer and can be checked on the identity (homology) with the known cDNA. In addition, by means of a homology retrieval on such a database by a computer for example, that which has a sequence similarity (homology) to the cDNA of a known protein/peptide can be freely picked up and subjected to an investigation of the function based upon the similarity (homology) with the sequence. However, there are still a large number of sequences which cannot be analyzed for the function thereof or wherein the function thereof cannot be deduced even by the above-mentioned checking and retrieval and they are the cDNA which is an object (target) of the method according to the present invention. The target cDNA which is a particular object of the present invention is any DNA wherein the in vivo biological function of the protein/peptide encoded by said cDNA can be hardly presumed nor inferred from the sequence information.

Representatively, the target cDNA used herein is a nucleotide sequence wherein the function thereof is not elucidated or, in other words, any DNA wherein the in vivo biological function of the protein/peptide encoded by said cDNA (including, for example, production of enzyme, production of growth factor, production of hormone, production of cytokine, production of differentiating factor, production of various gene products such as chemotaxic factor promoting the migration of leukocyte, protein increasing the phagocytic ability or bacteriocidal ability of leukocyte, lymphocyte growth factor, T cell activating factor, T cell growth factor, antigen-specific inhibiting factor specifically acting on immune system and antigen-nonspecific inhibiting factor, changes on the cell surface including, for example, formation of extracellular matrix, production of receptor protein, production of adhesion molecules, etc., changes in second messenger level, etc.) is ambiguous, particularly unknown.

In the probing method of the present invention, one or more cDNAs may be used. More preferably, such cDNA may include a cDNA library containing one or more said cDNAs and derived from organs (for example, brain, lung, stomach, intestine, liver, kidney, pancreas, spleen, bone marrow, lymph node, etc.) of warm-blooded animals (for example, rats, mice, guinea pigs, swine, sheep, cattle, monkeys, human being, etc.) and the like. Such a cDNA library may be prepared from the organs of the above-mentioned animals by a known method per se or by a method similar thereto but a commercially-available one may be used as well. Especially from a viewpoint of development of pharmaceuticals, it is preferred to use a cDNA library derived from human being. In conducting an analysis of the nucleotide sequence, the cDNA clone contained in the library may be treated randomly or that may be conducted after a selection by hybridization using a suitable probe or after an amplification by PCR techniques. It is also possible to elucidate the function in accordance with the present invention based upon the nucleotide sequence extracted from the database in which nucleotide sequences of cDNA etc. are accumulated. Particularly, the cDNA derived from human being may be used.

In obtaining a cDNA coding for a novel protein/peptide which functions in a specific tissue or cell, it is possible to systematize the function analysis by conducting the sequencing of the nucleotide sequence, the homology retrieval by a computer, the design of antisense oligonucleotide and the synthesis of antisense oligonucleotide by means of an online system. When various elucidations of functions of a variety of cDNAs are processed simultaneously, it is possible to investigate a novel useful protein/peptide in an efficient manner. It is also possible for the selection of the assessment system to investigate the tissue-specificity of said protein/peptide by conducting northern blotting or RT (Reverse Transcriptase)-PCR using the oligonucleotide prepared based upon said cDNA or said partial sequence. Alternatively, instead of the above, it is possible to find a cDNA library derived from the tissue wherein said cDNA is specifically contained by checking the database.

Preferably, an example of the cDNA used in the probing method according to the present invention is a cDNA which codes for about 1% to 100%, preferably about 10% to about 100% or, more preferably, from about 20% to 100% of the amino acid sequence of protein [cf. FIG. 1]. The partial sequence of said cDNA is a nucleotide sequence of about 0.1% to 99%, preferably about 1% to 50% or, more preferably, about 1% to 10% of the entire nucleotide sequence of the above-mentioned cDNA wherein a nucleotide of said DNA is partially sequenced and, usually, it comprises not less than about 10, preferably not less than about 30 and, more preferably, not less than about 100 nucleotide residues [cf. FIG. 1].

An example of the target cDNA used herein is a cDNA which codes for about 1% to 100% of the whole amino acid sequence of a certain protein or peptide and in which only a partial nucleotide sequence (for example, about 0.1 to 99% of the whole nucleotide sequence) of said cDNA is sequenced and, in addition, the function of said cDNA (or the function of the protein or peptide encoded by said cDNA) is not elucidated yet.

The antisense oligonucleotide used for the probing method of the present invention is any as long as it has a nucleotide sequence substantially complementary (hybridizable) to the partial sequence of cDNA. The term "substantially hybridizable oligonucleotide" means an oligonucleotide which is capable of hybridizing to the target cDNA or other related polynucleotides so as to form a double strand, to block transcription, or to affect biological functions thereof. In that case, the sequence may be complementary to the entire sequence of said partial nucleotide sequence or may be complementary to a portion of said partial nucleotide sequence. An example is an oligonucleotide which is complementary (substantially hybridizable) to about 0.1% to 99%, preferably about 1% to 10%, of said partial sequence of the above-mentioned target cDNA. Another example of the antisense oligonucleotide applicable is an oligonucleotide having, usually, about 3 to 100, preferably about 10 to 100, more preferably about 10 to 50 or, still more preferably, about 10 to 30 bases (nucleotides) in the sequence. It is particularly preferred that the partial sequence of said cDNA is a partial sequence at the 5'-terminal region of the full-length target cDNA or, in other words, it is a partial sequence which codes for the N-terminal site of a certain protein or peptide. This is because it has been known that, when an mRNA wherein its superstructure (or higher structure) is not elucidated is used as a target in an antisense technique, the expression of protein can be efficiently inhibited if the translation initiation region at the 5'-upstream thereof is blocked by an antisense oligonucleotide. Said cDNA partial sequences may include any regardless of those containing the 5'-end of the full-length target cDNA and those free from the 5'-end thereof. The sequence may contains about 1% to about 50% 5'-regions of the full-length target cDNA, preferably about 1% to about 10% 5'-regions thereof, or sequences within 100 bases including its initiation codon.

The relationship between the target and oligonucleotides complementary to at least a portion of the target, specifically hybridizable with the target, is denoted as "antisense". The antisense oligonucleotides may be polydeoxynucleotides containing 2'-deoxy-D-ribose, polyribonucleotides containing D-ribose, any other type of polynucleotide which is an N-glycoside of a purine or pyrimidine base, or other polymers containing nonnucleotide backbones (e.g., protein nucleic acids and synthetic sequence specific nucleic acid polymers commercially available) or nonstandard linkages, providing that the polymers contain nucleotides in a configuration which allows for base pairing and base stacking such as is found in DNA and RNA. They may include double- and single-stranded DNA, as well as double- and single-stranded RNA and DNA:RNA hybrids, and also include, as well as unmodified forms of the polynucleotide or oligonucleotide, known types of modifications, for example, labels which are known to those skilled in the art, "caps", methylation, substitution of one or more of the naturally occurring nucleotides with analogue, internucleotide modifications such as, for example, those with uncharged linkages (e.g., methyl phosphonates, phosphorotriesters, phosphoramidates, carbamates, etc.) and with charged linkages or sulfur-containing linkages (e.g., phosphorothioates, phosphorodithioates, etc.), those containing pendant moieties, such as, for example, proteins (including nucleases, nuclease inhibitors, toxins, antibodies, signal peptides, poly-L-lysine, etc.) and saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., alpha anomeric nucleic acids, etc.). The terms "nucleoside", "nucleotide" and "nucleic acid" will include those moieties which contain not only the known purine and pyrimidine bases, but also other heterocyclic bases which have been modified. Such modifications include methylated purines and pyrimidines, acylated purines and pyrimidines, or other heterocycles. Modified nucleosides or nucleotides will also include modifications on the sugar moiety, e.g., wherein one or more of the hydroxyl groups are replaced with halogen, aliphatic groups, or are functionalized as ethers, amines, or the like.

The antisense oligonucleotide of the present invention is RNA, DNA or a modified nucleic acid. Examples of modified nucleic acid are, but not limited to, degradation-resistant sulfurized and thiophosphate derivatives of nucleic acids, and poly- or oligonucleoside phosphoramidates. Preferred design modifications of the antisense oligonucleotides of the present invention are modifications that are designed to:

(1) increase the intracellular stability of the oligonucleotide;

(2) increase the cellular permeability of the oligonucleotide;

(3) increase the affinity of the oligonucleotide for the target sense strand; or (4) decrease the toxicity (if any) of the oligonucleotide. The nucleotide sequences may contain altered or modified sugars, bases or linkages, be delivered in specialized systems such as liposomes, microspheres or by gene therapy, or may have attached moieties. Such attached moieties include polycationic moieties such as polylysine that act as charge neutralizers of the phosphate backbone, or hydrophobic moieties such as lipids (e.g., phospholipids, cholesterols, etc.) that enhance interaction with cell membranes or increase uptake of the nucleic acid. Preferred lipids that may attached are cholesterols or derivatives thereof (e.g., cholesteryl chloroformate, cholic acid, etc.). The moieties may be attached at the 3' or 5' ends of the nucleic acids, and also may be attached on a base, sugar, or internucleotidic linkage. Other moieties may be capping groups specifically placed at the 3' or 5' ends of the nucleic acids to prevent degradation by nuclease such as exonuclease, RNase, etc. Such capping groups include, but are not limited to, hydroxyl protecting groups known to those skilled in the art, including glycols such as polyethylene glycols, tetraethylene glycol and the like.

Figure 2:
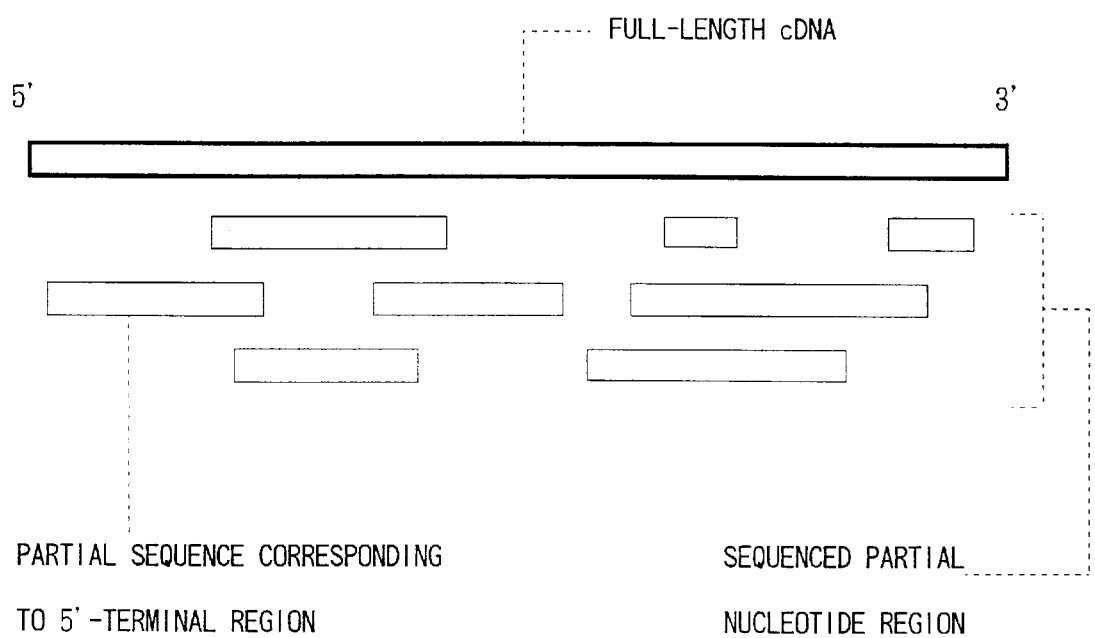
FIG. 2 illustrates a partial sequence corresponding to the 5'-terminal region of full-length cDNA model.

It is preferred, as shown in FIG. 2, that a cDNA group wherein the partial nucleotide(s) is(are) sequenced is investigated to presume the domain near the 5'-terminal and an antisense oligonucleotide substantially complementary to the partial sequence of cDNA corresponding to said region near the 5'-terminal is used. Such an oligonucleotide may be any of that which is manufactured according to known procedures, that which is manufactured by a novel method or that which is already mentioned in literatures or in patents as long as said oligonucleotide exhibits the above-mentioned properties. More preferably, the antisense oligonucleotide may include an antisense oligonucleotide mentioned in F. Eckstein, Angew. Chem., 6, 431(1989); F. Eckstein et al., Biochemistry, 23, 3443(1984); J. W. Stec et al., J. Am. Chem. Soc., 106, 6007(1984); F. Eckstein et al., Ann. Rev. Biochem., 54, 367(1985); P. S. Millar et al., Biochemistry, 18, 5134(1979); P. S. Millar et al.,Biochimie, 67, 769(1985); P. O. P. Ts'O et al., Ann. N.Y. Acad. Sci., 507, 220(1988), etc. Examples of the antisense oligonucleotide are phosphorothioate antisense oligonucleotide, alkyl phosphonate (e.g., methyl phosphonate) antisense oligonucleotide, alkoxy phosphate antisense oligonucleotide or phenyl phosphonate antisense oligonucleotide, derivatives thereof, etc. Preferred examples of the antisense oligonucleotide used herein are those having 1–300, preferably 1–200, more preferably 1–100, still more preferably 1–50 or, particularly preferably, 4–40 bases (nucleotides). More preferred examples of the antisense oligonucleotide are those having 4–35, more preferably 4–25 or, particularly preferably, 6–20 bases.

It is preferred that the antisense oligonucleotide used for the probing method of the present invention is an oligonucleotide capable of inhibiting the expression of a protein or peptide encoded by the target cDNA when said oligonucleotide is added to an assessment system for biological function wherein said protein or peptide is expressible, as will be mentioned herein below. For example, it is preferred that the oligonucleotide has a property of inhibiting the expression of said protein or peptide usually to an extent of about 20% to 100%, preferably about 30% to 100% or, more preferably, about 50% to 100%. Incidentally, that which is able to result in a substantially detectable change may be preferably used.

Said antisense oligonucleotide is added to the assessment system for the biological function after adjusting to a concentration whereby an expression of the target DNA can be inhibited or, particularly, transcription or translation of mRNA which is complementary to cDNA can be inhibited. For example, it is preferred that said antisense oligonucleotide is added to the cell culture liquid usually at the concentration of about 1 μmole to about 50 μmoles or, preferably, about 10 μmoles to about 30 μmoles.

In the probing method of the present invention, the assessment system wherein the protein or peptide encoded by cDNA is expressible stands for a system wherein the above-mentioned target cDNA can be expressed such as a system wherein the DNA coding for the protein or peptide in which its function is ambiguous(particularly unknown) can be expressed and the system wherein the change of the biological action upon expression of said protein or peptide can be evaluated or measured. Preferably, it is a system in which the genome DNA corresponding to said cDNA can be expressed whereby the change in the biological function (or change of biological action) can be evaluated or detected. An example is a culture system of the cell which may have expressed the protein or peptide encoded by the target cDNA. Examples of the cell are a cell group such as nerve cell, bone cell, muscle cell, blood vessel cell, endocrine cell, lymphocyte and reticuloendothelial cell as well as various cells and, more particularly, they are smooth muscle cell, endothelial cell, fibroblast, epithelial cell, blood cell and the like. Other examples are culture systems of various organs. Examples of the cell used for the probing system are a cell derived from the tissues which constitute epidermis, mucous membrane, exocrine gland, endocrine gland, lung, digestive organ, urinary/genital gland, genital cell, liver, fat tissue, connective tissue, blood vessel, muscle, hematocyte, bone marrow, nerve, etc. and an established cell strain (cell line) or a primary cultured cell from the above-mentioned tissues of either normal or tumorized state. When the expression site or expression cell which is complementary to said cDNA can be clarified by conducting an investigation by northern blotting, RT-PCR or database retrieval, the cell which is applicable to said assessment system may be selected therefrom based upon the resulting information.

In selecting an assessment system for the biological function in the probing method of the present invention, it is recommended to use a cell line in which expression of the protein encoded by the target cDNA is estimated through referring to a homology retrieval between the sequenced partial nucleotides of the target cDNA and known DNA sequences or through presumption of the cell specificity, the disease specificity, etc. from the property of the DNA library wherefrom the cDNA is obtained. It is also preferred to use a cell in which the disease wherein the target cDNA participates is significantly developed or is able to develop. For example, when the target cDNA is presumed to code for a bone growth factor, a bone cell culture system may be selected while, when the target cDNA is presumed to code for a nerve cell growth factor, a nerve cell culture system may be selected. As a result of the use of such a cell, the change in the biological function (change of the biological action) upon addition of an antisense oligonucleotide can be clearly assessed.

In the probing method of the present invention, assessment of the change in the biological function refers to detecting, measuring or observing the change of the biological action (change in the biological function such as a production of gene products in the cells used, promotion or inhibition of production of said gene products, changes on the surface of the cell, changes in the second messenger level, etc.) when the above-mentioned antisense oligonucleotide is added to the above-mentioned assessment system for the biological function to inhibit the expression of the target DNA. It particularly means to detect, to measure or to observe the changes in biological functions (such as a production of protein/peptide, a production of the second messenger level, changes on the cell surface, morphological changes, etc.) when the above-mentioned antisense oligonucleotide is added and transcription, translation, etc. of the mRNA having a sequence which is substantially complementary (hybridizable) to said antisense oligonucleotide is inhibited. Examples of the change in the biological function are a promotion or an inhibition of the production of enzyme, endocellular matrix and adhesion molecule (or factor), transcription controlling factor, growth factor, hormone, cytokine, differentiating/inducing factor, chemotaxic factor, neurotransmitter, etc. as well as morphological change such as elongation of neurite, shrinking or extension of cells and formation and disappearance of intracellular granules. Besides those, opening-and-closing of ion channel and changes in cell membrane potentials caused thereby, changes in the pH both inside and outside the cells or activation and inactivation of intracellular information transmittance system caused via various receptor protein as well as primary promotion and inhibition of production of various second messengers (such as cAMP, cGMP, inositol phosphate metabolites, diacylglycerol, intracellular calcium ion and arachidonic acid metabolites) and secondarily induced phosphorylation and dephosphorylation of various proteins are important index targets for probing the function too.

Examples of the gene products are various factors specifically related to amplification and differentiation or gene expression controlling factors in cells such as growth factor, hormone, cytokines, chemotaxic factor promoting the migration of leukocyte, protein increasing the phagocytic ability or bactericidal ability of leukocyte, lymphocyte growth factor, T cell activating factor, T cell growth factor, antigen-specific inhibiting factor specifically acting on an immune system, antigen-nonspecific inhibiting factor, etc. as well as various gene products corresponding to various enzymes and regulatory factors.

Examples of the change on a cell surface are a cell surface change including production of receptor protein, production of adhesion molecule, etc. or an extracellular change including formation of extracellular matrix, etc. Examples of a change in an intracellular second messenger are liberation of arachidonic acid metabolites, liberation of acetylcholine, liberation of $Ca^{+2}$, production of cAMP, production of cGMP, formation of inositol phosphate metabolites, a change in cell membrane potentials, phosphorylation of protein, activation of c-fos, a change in pH, etc.

In order to make such a change in biological function more easily observable, the cell which is used for the assessment system may be pretreated with a suitable inhibitor (e.g., proteinase inhibitor, phosphorylase inhibitor, ion channel inhibitor, etc.) or with a suitable activator (e.g., forskolin, phorbol ester and retinoic acid). When it is entirely impossible to foresee the expression site and function, then a representative cell or biological function assessment system is selected from the above and they may be systematically assayed for probing the biological function. Alternatively, attention is paid only to specific cells or a biological function and then they may be exclusively assayed.

In evaluating the biological function, a change in the cell to which the antisense oligonucleotide is added may be directly measured or observed or the measurement/observation may be conducted as a change on other cells caused by a supernatant fluid or an extract from culture of those cells. When the supernatant fluid of the extract of the cells is used, it may be concentrated and purified and, with an object of preventing the decomposition of the contained substance during the course of the assay, various inhibitors for the enzyme may be added.

With regard to a method for detecting the production of the above-mentioned gene products, immunological means such as ELISA and measurement of enzymatic activity as well as other simple means may be advantageously used. Such means may also be referred to each of the series of "Methods in Enzymology, Academic Press, Inc." for example and the descriptions therein are included in this specification as the references.

When the gene product is a nerve cell growth factor and the like, the cell extract or supernatant liquid, for example, is recovered, concentrated or diluted to a suitable concentration, added to nerve cells and the growth of said nerve cells is observed. Observation of growth of nerve cells at that time may be either a morphological observation of the nerve cells or may be a measurement of liberation of arachidonic acid metabolites, liberation of acetylcholine, liberation of $Ca^{+2}$, production of cAMP, production of cGMP, production of inositol phosphate metabolites, changes in cell membrane potential, phosphorylation of protein, activation of c-fos, changes inpH, production of gene products (e.g., cell growth factor, cell differentiation factor, cell living factor, chemotaxic factor which promotes the migration of leukocytes, protein which promotes the phagocytic ability or bactericidal activity of leukocyte, lymphocyte growth factor, T cell activating factor, T cell growth factor, antigen-specific inhibiting factor which specifically acts on immune system, antigen-nonspecific inhibiting factor, etc.) in the nerve cell.

Examples of the method for detecting above-mentioned changes on the cell surface are a method in which cell surface is observed under a microscope, a method in which the gene products from the above-mentioned culture are separated, isolated and purified and a method in which production of a receptor protein by a ligand binding experiment is detected.

In a method for detecting the change in the above-mentioned second messenger level, a measurement may be carried out by a known method or a commercially available assay kit. Preferably, the cell in which the protein encoded by the partial sequence of said cDNA is expressed is at first cultured in a multiwell plate or the like. In conducting a measurement of the change in the function, it is previously substituted with a fresh medium or with a suitable buffer which is nontoxic to the cells and, after an incubation for certain period, the cell extract or supernatant liquid is recovered and the resulting product is determined by a method corresponding thereto. When the production of the substance which is to be an index target (e.g., arachidonic acid, metabolites production, etc.) is difficult to identify due to the enzyme contained in the cells, the assay may be carried out after adding an inhibitor against said enzyme. Incidentally, with respect to the activity of inhibiting the cAMP production, etc., it may be detected as an inhibitory action for the production to the cells wherein the basic production is promoted by forskolin or the like.

Thus, the specific procedures in accordance with a probing method of the present invention will be as follows:

(1) an antisense oligonucleotide which is complementary to a part of the target cDNA where a nucleotide of said DNA is partially sequenced is designed and synthesized. Said antisense oligonucleotide may be that which corresponds to any part of said cDNA but, preferably, it is an antisense oligonucleotide having a partial sequence at the 5'-terminal region of a full-length cDNA (or a coding DNA sequence including 5'-flank) and being complementary to said partial sequence.

Said cDNA may be that wherein its partial nucleotide sequence is newly sequenced or that which is extracted from a database. That in which the information on tissue specificity, homology, etc. is collected by excluding the cDNA coding for known protein/peptide as a result of homology retrieval between the partial sequence of said target cDNA with the known DNA is preferred. A preferred antisense oligonucleotide prepared includes one or more which is/are selected from the partial sequence (more preferably, the partial sequence at the 5'-terminal region of the full-length cDNA) of said cDNA. Such an antisense oligonucleotide may be a mixture of several types of them. In the meanwhile, a reverse sequenced oligonucleotide used as a control is synthesized and prepared.

(2) Then a selection of the assessment system is conducted. When it is expected that the protein or peptide encoded by said cDNA is expressed in a specific cell or organ as a result of an earlier investigation for a cell specificity or a disease specificity of the protein or peptide encoded by the target cDNA by, for example, means of a homology retrieval of the partial sequence of said cDNA with the known DNA, then it is preferred to select an assessment system for the biological function using such a cell or organ (for example, the culture system of a cell having a possibility of expressing the protein encoded by said cDNA). As a result thereof, an investigation for the function with a far higher possibility is now possible. For example, a selection of the assessment system is carried out by referring to the information such as a homology or tissue specificity obtained in (1).

(3) Then, the antisense oligonucleotide prepared as such is added to the assessment system for the biological function. After that, it is checked whether the change in the biological function takes place in said assessment system. Preferably, this antisense oligonucleotide is randomly added to the assessment systems of as many as possible and it is checked whether the change in the biological function takes place. In order to confirm whether the change in the biological function is caused by an antisense effect, it is desirable to investigate the system to which a reverse sequenced oligonucleotide is added as a control too.

(4) When the change in the biological function at that time is evaluated, the biological function which changes by adding the antisense oligonucleotide thereto can be confirmed.

For example, when the selected assessment system for the biological function is an assessment system in which the protein or peptide encoded by said cDNA is not expressed (particularly when it is an assessment system in which an mRNA complementary to said cDNA is not expressed) or, for example, when it is a culture system of the cell wherein the protein or peptide encoded by said cDNA is not expressed, then there is no change in the biological function even when antisense oligonucleotide is added thereto. In that case, even if a reverse sequenced oligonucleotide is added, it is usual that there is no change in the biological function.

On the other hand, when the selected assessment system for the biological function is an assessment system wherein the protein or peptide encoded by said cDNA can be expressed (particularly when an assessment system wherein an mRNA complementary to said cDNA is expressed) or, for example, when a culture system of the cell which expresses the protein or peptide encoded by said cDNA, then the expression of said protein or peptide (for example, a production of the protein/peptide encoded by said cDNA) is inhibited and, therefore, there is a change in the biological function. In addition, an expression of the genome DNA corresponding to said cDNA is inhibited for example and, therefore, there is a change in the biological function. At that time, in a system to which a reverse sequenced oligonucleotide is added, there is usually no change.

(5) As a result thereof, it is now clarified that the biological function which is changed by addition of an antisense oligonucleotide is a function of said cDNA wherein the nucleotide of said DNA is partially sequenced. To be more specific, it is now clear that the resulting function is a function that the protein/peptide (encoded by the cDNA wherein the nucleotide of said DNA is partially sequenced) exhibits.

One of the characteristic features of the present invention is that, even when a sequence similarity of said partial sequence of the cDNA wherein the nucleotide of said DNA is partially sequenced with a known DNA is low, it is now possible to find out the function. In addition, when it is expected that the protein or peptide encoded by said cDNA is expressed in a specific cell or organ as a result of an earlier investigation for a cell specificity or a disease specificity of the protein or peptide encoded by cDNA wherein the nucleotide of said DNA is partially sequenced by, for example, means of a homology retrieval of the partial sequence of said cDNA with the known DNA, then it is possible to assess the biological function using such a cell or organ and to conduct an investigation for the function with a far higher possibility. Needless to say, it is easily, simply and quickly confirmed in accordance with the present invention whether said DNA exhibits a biological function or not. Consequently, it can be also utilized for the confirmation of the DNA having no biological function.

Specifically detailed description of embodiments according to the method of the present invention will be given hereinafter.

Embodiment 1

Diseases related to bones such as osteoporosis develop when a balanced relation between bone resorption and formation in bone tissues conducting an active metabolism is broken off. Said bone resportion and formation are conducted by the cells called osteoclasts and osteoblasts, respectively, which are characteristic to bones. It is very important to elucidate the formation process of osteoclasts and osteoblasts and also the action mechanism for controlling the function of the formed cells since they are associated with the therapy of diseases related to bones.

The osteoclast having an ability of bone resorption is a polynuclear giant cell and it has been known that it grows from a mononuclear hemotopoietic stem cell through the steps of differentiation and fusion. Its characteristic features are that (1) it has an acid phosphatase activity resistant to tartaric acid; (2) it has a calcitonin receptor; (3) it is multinuclear; and (4) it absorbs a calcified substrate. The differentiating steps of the osteoclast are classified into a step in which mononuclear cells gain the characters of (1) and (2) and a step in which they are fused and, finally, they are activated to the cell having an ability of bone resorption.

When bone marrow cells are cultured in vitro for long time, cells having the above-mentioned character of osteoclast are formed. Alternatively, when spleen cells are cultured together with osteoblasts or with undifferentiated mesenchymal cells, osteoclasts are formed too. Now it is possible conduct the following for the cDNA (which is expressed specifically and abundantly in bone tissues and whose structure is partially sequenced) using the osteoclasts cultured as such:

(1) to investigate the 5'-terminal region by conducting a comparison of partial structures, (2) to synthesize an antisense oligonucleotide comprising 10–30 mer (preferably, 15–30 mer) at said site and an oligonucleotide having a reverse sequenced orientation thereto;

(3) to construct a system in which those nucleic acid oligomers are added to a osteoclast culture system and also a system in which they are not added;

(4) to observe the forming processes of differentiation and fusion of said osteoclasts; and (5) to confirm that, when an inhibition against the growth of osteoclasts is clearly noted in the system to which the antisense oligonucleotide is added, the cDNA is a cDNA which codes for the novel gene product necessary for the differentiating and fusing processes of osteoclasts. On the other hand, when an experimental system in which osteoblasts are used is constructed instead of the use of osteoclasts as mentioned above, it is possible to confirm the DNA which codes for the gene product necessary for the differentiating and fusing processes of osteogenesis.

Thus, when a nucleotide of the DNA is partially sequenced, the function of said cDNA, particularly the function of the protein or peptide coded by said DNA, can be elucidated and assessed using the antisense oligonucleotide as mentioned above.

The cDNA whose function can be probed by the method of the present invention is subjected to a further sequencing whereby it is possible to determine a full-length nucleotide sequence of said cDNA.

When it is clarified that said cDNA only partially codes for the protein or peptide, the deficient part can be newly cloned using a known genetic engineering technology whereby a full-length cDNA can be cloned which codes for the entire protein. An example of the means for cloning a full-length cDNA is a hybridization technique which is disclosed, for example, in "Molecular Cloning", 2nd Edition (edited by J. Sambrook et al., Cold Spring Harbor Laboratory Press, 1989). When a commercially available library is used, a protocol mentioned in the directions attached thereto are to be followed.

After obtaining a full length cDNA, an antisense oligonucleotide is prepared based upon the sequence of said cDNA and the method for probing the function in accordance with the present invention is applied (for example, a method in which the full length cDNA is added to an assessment system for the biological function used for the probing method of the present invention wherein a nucleotide of said DNA is partially sequenced is applied, etc.) whereupon it is possible to reconfirm the function of the protein/peptide encoded by said full-length cDNA. After the coding region for the full-length protein/peptide is found, said protein/peptide is manufactured by a known DNA-expression method or by a chemical peptide synthesis whereby the function can be reconfirmed too. It is to be particularly noted that, when an antibody against said protein/peptide manufactured above is prepared and added to an assessment system for the biological function like an antisense oligonucleotide, the function of said protein/peptide can be reconfirmed as well.

The cloned full-length cDNA may be used as it is or, if desired depending upon the purpose, it may be used after digesting with a restriction enzyme or after adding a linker thereto. Said DNA may have ATG as a translation initiation codon at its 5'-terminal side or TAA, TGA or TAG as a translation termination codon at its 3'-terminal side. Those translation initiation and termination codons may be added using a suitable synthetic DNA adaptor.

The cDNA wherein its function is elucidated or the protein which is encoded by said cDNA may be used as a pharmaceutical agent as it is or may be used as a reagent for screening the pharmaceuticals depending upon its function. In addition, the antisense oligonucleotide per se which is prepared for probing the function may be used as a pharmaceutical agent or a reagent as well. Some specific uses will be given as hereinafter although they are just examples and, needless to say, there are still many other areas to which the present invention is applicable.

(cDNA codes for an inhibitor to a certain disease]

When the protein encoded by cDNA is a cancer-inhibiting substance, the protein is manufactured from cDNA by a known DNA expressing method whereby said protein can be used as an anti-cancer drug. Said cDNA per se can be used as a gene remedy for cancer too.

(the protein/peptide encoded by cDNA functions as a receptor)

The receptor protein manufactured by cDNA of a full length is useful as a reagent for investigating or determining a ligand to said receptor. It is further possible to conduct a screening of a compound or a salt thereof which inhibits the binding of said receptor protein with the ligand. Such a compound includes that which exhibits a cell-stimulating activity through a receptor (the so-called receptor agonist) and that which does not exhibit such a cell-stimulating activity (the so-called receptor antagonist).

(cDNA codes for a G protein coupled receptor protein)

(1) It is useful in a method for determining a ligand to a G protein coupled receptor protein.

A G protein coupled receptor protein manufactured from said cDNA or a partial peptide thereof is useful as a reagent for investigating or determining a ligand to the G protein coupled receptor protein.

(2) It is useful in a screening method for the compound which inhibits a binding of the G protein coupled receptor protein with the ligand.

When the G protein coupled receptor protein or a partial peptide thereof is used or when an expression system of a recombinant receptor protein is constructed and the receptor binding assay system using said expression system is used, it is possible to screen for a compound (for example, peptide, protein, nonpeptidic compound, synthetic compound, fermented product, etc.) which inhibits the binding of the ligand with the G protein coupled receptor protein or its salt. Such compounds include a compound (for example, the so-called G protein coupled receptor agonist) having a ligand-like action through a G protein coupled receptor (for example, liberation of arachidonic acid metabolites, liberation of acetylcholine, liberation of intracellular $Ca^{+2}$, generation of intracellular cAMP, generation of intracellular cGMP, production of inositol phosphate metabolites, change in cell membrane potential, phosphorylation of intracellular protein and an activity which promotes or inhibits the activation of c-fos) and a compound (the so-called G protein coupled receptor antagonist) which has no said ligand-like action but inhibits the ligand activity.

(3) It is useful as a preventive and therapeutic agent for diseases caused by the deficiency of G protein coupled receptor proteins.

When a ligand to the G protein coupled receptor protein is clarified in the above-mentioned method (1), the DNA which codes for the G protein coupled receptor protein may be used, depending upon the action of said ligand, as a preventive and therapeutic agent for the disease caused by a deficiency in the G protein coupled receptor protein.

For example, when there is a patient to whom the physiological action of the ligand cannot be expected because of a decrease in the G protein coupled receptor protein in vivo, then (a) cDNA which codes for the G protein coupled receptor protein is administered to said patient for its expression or (b) the cDNA which codes for the G protein coupled receptor protein is inserted into brain cells or the like and expressed followed by transplanting said expressing brain cells to said patient whereby the amount of the G protein coupled receptor protein in the brain cells of said patient increases and the action of the ligand can be fully achieved. Accordingly, the cDNA which codes for the G protein coupled receptor protein can be used as a safe and less toxic preventive and therapeutic agent of the present invention for the G protein coupled receptor protein-deficient disease.

Hereinabove, a description was made on the G protein coupled receptor protein and DNA coding therefor but the present invention is applicable to receptor proteins which are not a G protein coupled type and also to DNA coding therefor too.

(the protein/peptide encoded by cDNA functions as a differentiating/growth factor for a certain type of cells)

When, for example, a certain type of cell growth depending upon said protein/peptide, then it is possible to inhibit the production of said protein/peptide by an antisense oligonucleotide or an antibody whereby the propagation of tumor cells derived from the above cell can be inhibited. In addition, compounds which inhibit said differentiating/ growth activity are screened whereupon the resulting screened compound can be used as an antitumor drug. In the case of a factor which induces a differentiation, it is possible, like a differentiation-inducing therapy for leukemia cells, to convert the tumor cells to their nontoxic state whereupon a therapy is achieved.

(the protein/peptide encoded by cDNA functions is an enzyme)

When a patient suffering from a metabolic disease induced by the insufficient function or deficiency of an enzyme is administered directly with said enzyme manufactured, for example, by a genetic engineering means or indirectly with an expressible gene vehicle prepared by inserting an full-length enzyme-encoding cDNA into a suitable expression vector, then the insufficient enzymatic activity can be supplemented.

(the protein/peptide encoded by cDNA functions as a hormone)

In order to control the insufficiency of the tissue/organ which is a target of the hormone action in a hormone deficient-disease, said protein/peptide manufactured either by a genetic engineering means or a chemical synthesis is directly administered to a patient or as an expression product obtainable in vivo through an expressible gene vehicle prepared by inserting an full-length hormone protein/ peptide-encoding cDNA into a suitable expression vector whereby the action of said hormone can be supplemented.

(the protein/peptide encoded by the cDNA is a chemotaxic factor)

In a therapy of a symptom caused by an induction of cells by chemotaxis, similar to neutrophils/monocytes in inflammation, a inhibiting compound or a salt thereof may be screened and used. Alternatively, an antisense oligonucleotide per se may be used for inhibiting such a chemotaxis.

(the protein/peptide encoded by cDNA functions in a formation of extracellular matrix or an adhesion molecule)

For example, it is possible to conduct a screening of a compound or a salt thereof which inhibits the function of extracellular matrix or adhesion molecule which functions in adhesion/infiltration of cells such as metastasis of tumor. In the case of extracellular matrix or adhesion molecule which is specific to a certain special cell, development of an antitumor drug quite specific to the tumor cells derived from such a cell may be expected. It is also possible to use the antisense oligonucleotide per se for inhibiting the adhesion/ infiltrat ion of them.

(the protein/peptide encoded by cDNA is a transcription control factor)

When the function is involved in a transcriptional factor for controlling the transcription of a specific gene, then it is possible to screen for a compound which inhibits the disease caused by an excessive expression of said gene. It is also possible to inhibit the expression of those genes using an antisense oligonucleotide per se. In addition, when the function is related to a factor which controls the transcription of the genes coding for the protein/peptide (e.g., growth factor, hormone, etc.) which is essential to a living body, it is possible to conduct a screening of a compound which promotes the expression/transcription of said genes.

The practice of the present invention will employ, otherwise indicated, conventional techniques of molecular biology, microbiology, recombinant DNA, pharmacology, immunology, biochemistry, bioscience, and medical technology, which are within the skill of the art. All documents, and publications mentioned herein, both supra and infra, are hereby incorporated herein by reference.

EXAMPLES

Described below are examples of the present invention which are provided only for illustrative purposes, and not to limit the scope of the present invention. In light of the present disclosure, numerous embodiments within the scope of the claims will be apparent to those of ordinary skill in the art.

Example 1

(1) Selection of cDNA with Unknown Function.

As a cDNA with unknown function, the cDNA wherein the partial nucleotide sequence represented by SEQ ID NO: 1 of the following:
GTAAGAGTTT GTGGAAGGAT TAACCTGCGC GCGC-
CGGGGT GGGTGCCTGT GCGGGGCGCG
CGGGGCGGGC GGCGGTGGGT GCCCGTGGGG
GCCAGGGTGA (SEQ ID NO: 1)
is sequenced is used.

(2) Procurement of Antisense Oligonucleotide.

Oligonucleotides are manufactured using a DNA synthesizer. They are antisense oligonucleotide (I) having a nucleotide sequence represented by SEQ ID NO: 2 corresponding to a nucleotide sequence of from 1st to 15th base region of SEQ ID NO: 1 cDNA; antisense oligonucleotide (II) having a nucleotide sequence represented by SEQ ID NO: 3 corresponding to a nucleotide sequence of from 51st to 65th base region of SEQ ID NO: 1 cDNA; antisense oligonucleotide (III) having a nucleotide sequence represented by SEQ ID NO: 4 corresponding to a nucleotide sequence of from 81st to 95th base region of SEQ ID NO: 1 cDNA; oligonucleotide (IV) having a nucleotide sequence represented by SEQ ID NO: 5 which is a reversed sequence to the antisense oligonucleotide (I); oligonucleotide (V) having a nucleotide sequence represented by SEQ ID NO: 6 which is a reversed sequence to the antisense oligonucleotide (II); and oligonucleotide (VI) having a nucleotide sequence represented by SEQ ID NO: 6 which is a reversed sequence to the antisense oligonucleotide (III).
(SEQ ID NO: 2) TCCACAAACT CTTAC (I)
(SEQ ID NO: 3) CCCCGCGCGC CCCGC (II)
(SEQ ID NO: 4) CTGGCCCCCA CGGGC (III)
(SEQ ID NO: 5) CATTCTCAAA CACCT (IV)
(SEQ ID NO: 6) CGCCCCGCGC GCCCC (V)
(SEQ ID NO: 7) CGGGCACCCC CGGTC (VI)

(3) Amount of the Oligonucleotide Used.

The amount of about 1 to about 50 micromoles or, preferably, about 10 to about 30 micromoles, of the oligonucleotide is used.

(4) Assessment System for the Biological Function.

The following three systems are used:
 (a) a system in which 10–30 micromoles of the antisense phosphorothioate (I)–(III) in the above-mentioned (2) are added to the assessment system;
 (b) a system in which 10–30 micromoles of the phosphorothioates of the reversed orientation of (IV)–(VI) mentioned in (2) are added; and
 (c) a system in which such an oligonucleotide derivative is not added.

(5) Assay.

Suitable amounts of the antisense oligonucleotide and the reversely-oriented oligonucleotide as mentioned in the above (2) and of crude brain extract which is a material for isolating the cDNA as mentioned in the above (1) are added to cultured glial cells, which are thereafter cultured for 24 to 48 hours, washed with a physiological saline water buffered with a Hanks' solution and immobilized with formalin (a 9:1 mixture of ethanol and formalin) for 15 minutes. After that, it is treated with 100% acetone for 30 minutes and 3% Tween 80 solution for one minute for four times. Then it is incubated in a phosphate buffered saline solution containing 2% bovine serum albumin (PBS with 2% BSA) at 37° C. for 1 hr. to block non-specific adsorbing sites, followed by incubation with PBS with 2% BSA, containing anti-GFAP serum (GFAP: glial fibrous acid protein) which is prepared from rabbit, at 37° C. for 1 hr. Next, after removing an excess of antisera by washing 4 times with PBS, it is incubated in PBS with 2% BSA, containing horseradish peroxidase (HRP)-labeled anti-rabbit IgG, at 37° C. for 1 hr. Finally, after removing an excess of anti-rabbit IgG by washing 4 times with PBS, only GFAP containing cells are stained with a commercially available peroxidase detecting reagent.

(6) Results of the Observation.

If significant changes are noted in numbers and shape of the astroglial cells (type I) in a system to which the antisense oligonucleotide is not added and in a system to which a reversely-oriented phosphorothioate is added while, in a system to which antisense oligonucleotide is added, there is no change in numbers and shape of the glial cells as a result of the observation under the microscope, then it is clarified that the protein encoded by cDNA having, as a partial sequence, a nucleotide sequence of SEQ ID NO: 1 is a growth factor for glial cells or a promoting factor for the growth of glial cells.

Example 2

(1) Procurement of Encoding cDNA with Unknown Function.

The cDNA wherein the partial sequence (SEQ ID NO: 8) of the following:

CGAGTGGACA GTGGCAGGCG GTGACTGAAT CTCCAAGTCT GGAAACAATA GCCAGAGATA GTGGCTGGGA AGCACCATGG CCAGAGTCCT GCAGCTCTCC CTGACTGCTC TCCTGCTGCC TGTGGCTATT GCTATGCACT CTGACTGCAT CTTCAAGAAG GAGCAAGCCA TGTGCCTG (SEQ ID NO: 8)

is known is used as a cDNA with unknown function.

(2) Preparation of Antisense Oligonucleotide.

Oligonucleotides are manufactured using a DNA synthesizer. They are antisense oligonucleotide (VII) having a nucleotide sequence represented by SEQ ID NO: 9 corresponding to a nucleotide sequence of from 1st to 15th base region of SEQ ID NO: 8 cDNA in the above (1); antisense oligonucleotide (VIII) having a nucleotide sequence represented by SEQ ID NO: 10 corresponding to a nucleotide sequence of from 71st to 85th base region of SEQ ID NO: 8 cDNA; antisense oligonucleotide (IX) having a nucleotide sequence represented by SEQ ID NO: 11 corresponding to a nucleotide sequence of from 140th to 154th base region of SEQ ID NO: 8 cDNA; oligonucleotide (X) having a nucleotide sequence represented by SEQ ID NO: 12 which is a reversed sequence to the antisense oligonucleotide (VI); oligonucleotide (XI) having a nucleotide sequence represented by SEQ ID NO: 13 which is a reversed sequence to the antisense oligonucleotide (VIII); and oligonucleotide (XII) having a nucleotide sequence represented by SEQ ID NO: 14 which is a reversed sequence to the antisense oligonucleotide (IX).

(SEQ ID NO: 9) GCCACTGTCC ACTCG (VII)
(SEQ ID NO: 10) TCTGGCCATG GTGCT (VIII)
(SEQ ID NO: 11) GAAGATGCAG TCAGA (IX)
(SEQ ID NO: 12) GCTCACCTGT CACCG (X)
(SEQ ID NO: 13) TCGTGGTACC GGTCT (XI)
(SEQ ID NO: 14) AGACTGACGT AGAAG (XII)

(3) Amount of the Antisense Oligonucleotide Used.

The amount of about 1 to about 50 micromoles or, preferably about 10 to about 30 micromoles, of the oligonucleotide is used.

(4) Evaluating System for the Biological Function.

In order to check whether the biological function of the protein/peptide encoded by said cDNA is involved in, for example, a factor which is related to a cell propagation, the following are prepared:

IMR-32 (human neuroblastoma), $C_6$ (glioblastoma of rat), ACHN (cell strain derived from human kidney cancer), HL-60 (cell strain from human promyelocytic leukemia), MCF-7 (human breast cancer cell), $GH_3$ (pituitary tumor of rat), Bowes (human melanoma) and HISM (cell derived from human smooth muscle).

Those are mere examples and there is no particular limitation for the animal species and original tissues used therefor. Those cells are inoculated in a flask for a cell culture and the following three systems are prepared:

(a) a system in which 10–30 micromoles of the antisense phosphorothioate of (VII) to (IX) in the above (1) are added;

(b) a system in which 10–30 micromoles of the reversely-oriented phosphorothioate of (X) to (XII) in (1) are added; and (c) a system in which none of such a phosphorothioate is added.

The phosphorothioate is added to a medium of a composition which is suitable to each of the cells, cultured for several days and then cultured for 24–48 hours in a medium in which a phosphorothioate is added to RPMI 1640 medium containing no serum. The supernatant liquid of the culture is recovered, concentrated by means of ultrafiltration or the like if necessary and added to those cells which are cultured in a multiwell plate for a cell culture. In the case of the above-mentioned cases for example, the supernatant liquid of IMR-32 cell culture is added to all of other cells. Measurement of the cell growth activity may be quantified by an incorporation of [$^3$H]thymidine or by the use of a commercially available kit for cell growth measurements.

(5) Results of the Observation.

In the above-mentioned assay, if propagation of the cell is noted in the system where no phosphorothioate is added and the system where reversely-oriented antisense phosphorothioate is added while, in the system where antisense phosphorothioate is added, propagation of the cell is not noted, then it is clarified that the protein/peptide encoded by the cDNA having a nucleotide sequence of SEQ ID NO: 8 as its partial sequence is a cell growth factor. It is also clarified that, if inhibition of a cell propagation is noted in the system where no phosphorothioate is added and in the system where a reversely-oriented antisense phosphorothioate is added while, in the system where the antisense phosphorothioate is added, said propagation-inhibiting activity is not noted, then it is clarified that the protein/peptide encoded by the cDNA having the nucleotide sequence of SEQ ID NO: 8 as its partial sequence is an inhibiting factor for the cell propagation.

Further, if inhibition of a cell propagation or a morphological change in the cell cultured with the above-mentioned object is noted in the system where no phosphorothioate is added or in the system where a reversely-oriented antisense phosphorothioate is added while, in the system where the antisense phosphorothioate is added, said inhibition of propagation or said morphological change is not noted, then it is clarified that the protein/peptide encoded by said cDNA having a nucleotide sequence of SEQ ID NO: 8 as its partial sequence is related to the propagation/differentiation of said cell.

The method for probing the function of cDNA in accordance with the present invention is a method in which the function of a specific cDNA (particularly the function of the protein/peptide encoded by cDNA where a nucleotide of said DNA is partially sequenced) can be elucidated, assessed, evaluated or analyzed from a library of cDNA where a nucleotide of said DNA is partially sequenced even in such an early stage that only the partial sequence of said cDNA is determined and it is a novel probing technique which is entirely nonobvious from the art which has been known.

Up to now, it has been very laborious not only to conduct a sequencing and analysis of all nucleotide sequences of cDNA regardless of the fact whether or not the function is important but also to construct a system where the cDNA in which the nucleotide sequence is sequenced is efficiently expressed.

However, in accordance with the method for probing the function according to the present invention wherein antisense technique are utilized, it is now possible to efficiently elucidate, assess, evaluate or analyze the function of the protein based upon full-length cDNA (encoding cDNA), even in such an early stage that its total nucleotide sequence is not sequenced yet, concerning the sequences of many cDNA's (particularly the cDNA wherein a nucleotide of said DNA is partially sequenced) in which the function is not elucidated yet. Thus, the method for probing the function of cDNA in accordance with the present invention provides a useful information for developing pharmaceuticals useful for a living body to the researchers throughout the world who are exclusively concerned with an elucidation of function of new cDNA in the area of genetic engineering and also with a development of pharmaceuticals and the like.

The cDNA whose function is assessed by a probing method of the present invention and the protein encoded thereby and also the antisense oligonucleotide prepared for probing the function are useful as pharmaceuticals per se and also as reagents for screening the pharmaceuticals depending upon the assessed function.

---

What is claimed is:

1. A method for probing an unknown function of a protein or peptide encoded by a cDNA, wherein said cDNA completely or partially codes for said protein or peptide, and wherein only a part of the nucleotide sequence of said cDNA is sequenced, which comprises:

(a) designing and synthesizing an antisense oligonucleotide which is complimentary to a part of the nucleotide sequence of said cDNA, wherein said antisense oligonucleotide is selected from the group consisting of polydeoxynucleotides containing 2'-deoxy-D-ribose, polyribonucleotides containing D-ribose, polynucleotides containing an N-glycoside of a purine or pyrimidine base and polymers containing (i) nonnucleotide backbones including protein nucleic acids and synthetic sequence-specific nucleic acid polymers, or (ii) nonstandard linkages, provided that the polymers contain nucleotides in a configuration which allows for base pairing and base stacking;

(b) assessing:
    (i) a biological cell function of said protein or peptide in the presence of said antisense oligonucleotide,
    (ii) a biological cell function of said protein or peptide in the presence of a reverse sequence oligonucleotide, and
    (iii) a biological cell function under conditions free from said antisense oligonucleotide; and (c) predicting the function of said protein or peptide based on a change in biological cell function identified in step (b).

2. The method according to claim 1, wherein said part of the cDNA nucleotide sequence is a segment positioned at the 5' terminal region of a full-length nucleotide sequence of said cDNA.

3. The method according to claim 1, wherein said nonstandard linkage is selected from the group consisting of methyl phosphonates, phosphotriesters, phosphoramidates, carbamates, phosphorothioates, and phosphorodithioates.

4. The method according to claim 1, wherein the change in biological cell function is a promotion of or an inhibition of production of an enzyme, extracellular matrix, adhesion molecule, transcription controlling factor, growth factor, hormone, cytokine, differentiation/induction factor, chemotaxic factor, or neurotransmitter.

5. The method according to claim 1, wherein the change in biological cell function is a production of a growth factor, hormone, cytokine, chemotaxic factor capable of promoting the migration of leukocyte, protein capable of increasing the phagocytosis or bacteriocidal ability of a leukocyte, lymphocyte growth factor, T cell activating factor, T cell growth factor, antigen-specific inhibiting factor specifically acting on an immune system, or antigen-nonspecific inhibiting factor.

6. The method according to claim 1, wherein the change in biological cell function is a change on the surface of the cell or a change outside the cell.

7. The method according to claim 1, wherein the change in biological cell function is:

an opening-closing of ion channel, a change in the cell membrane potential, a change in the intracellular or extracellular pH, an activation or inactivation of an intracellular signal transduction system mediated by various receptor proteins; or a primary promotion or inhibition of production of a second messenger as well as secondarily induced phosphorylation or dephosphorylation of a protein.

8. The method according to claim 1, wherein the change in biological cell function is a liberation of arachidonic acid, liberation of acetylcholine, liberation of $Ca^{+2}$, generation of cAMP, generation of cGMP, production of inositol phosphate metabolities, change in cell membrance potential, phosphorylation of a protein, activation of c-fos, or change in pH.

9. The method according to claim 1, wherein the change in biological cell function is a morphological change of the cell.

* * * * *